United States Patent [19]

Neale et al.

[11] Patent Number: 5,688,782
[45] Date of Patent: Nov. 18, 1997

[54] MEDICAMENTS FOR TREATING RESPIRATORY DISORDERS

[75] Inventors: Philip John Neale; Anthony James Taylor, both of Ware, Great Britain

[73] Assignee: Glaxo Group Limited, Greenford, Great Britain

[21] Appl. No.: 458,241

[22] Filed: Jun. 2, 1995

Related U.S. Application Data

[62] Division of Ser. No. 256,294, filed as PCT/EP93/00223 Feb. 2, 1993.

[30] Foreign Application Priority Data

Feb. 6, 1992 [GB] United Kingdom ............ 92 02519

[51] Int. Cl.$^6$ .................. A61K 31/56; A61L 9/04
[52] U.S. Cl. ............................ 514/180; 424/45
[58] Field of Search ...................... 514/180; 424/45

[56] References Cited

U.S. PATENT DOCUMENTS 4,347,236  8/1982  Tanskanen ................. 424/45
4,810,488  3/1989  Jinks ........................... 424/45
4,866,051  9/1989  Hunt et al. ................. 514/180

FOREIGN PATENT DOCUMENTS

A-2 076 422  12/1981  United Kingdom.
A-2 107 715  5/1983  United Kingdom.
WO-A-92 06675  4/1992  WIPO.

*Primary Examiner*—Marianne M. Cintins
*Assistant Examiner*—Dwayne C. Jones
*Attorney, Agent, or Firm*—Bacon & Thomas

[57] ABSTRACT

This invention relates to aerosol formulations of use for the administration of medicaments by inhalation, in particular a pharmaceutical aerosol formulation which comprises: (a) beclomethasone dipropionate monohydrate, the particle size of substantially all the monohydrate being less than 20 microns; (b) at least 0.015% by weight of the formulation of water in addition to the water of crystallization associated with the monohydrate; and (c) a fluorocarbon or hydrogen-containing chlorofluorocarbon propellant. A method of treating respiratory disorders which comprises administration by inhalation of an effective amount of a pharmaceutical aerosol formulation as defined is also described.

18 Claims, No Drawings

MEDICAMENTS FOR TREATING RESPIRATORY DISORDERS

This application is a division of application Ser. No. 08/256,294, filed Jul. 12, 1994, which is a 371 of PCT/EP93/00223, filed on Feb. 2, 1993.

BACKGROUND OF THE INVENTION

1. Field of the Invention

This invention relates to improvements in or relating to pharmaceutical compositions comprising a beclomethasone ester. In particular the invention relates to novel aerosol formulations of use in the administration of beclomethasone dipropionate by inhalation.

2. Description of the Prior Art

Beclomethasone dipropionate is 9α-chloro-16β-methyl-1,4-pregnadiene-11β,17α-21-triol-3,20-dione 17α,21-dipropionate and may be represented by the formula (I)

The corticosteroid of formula (I) is known to exhibit topical antiinflammatory activity and is described and claimed in GB 1047519. In the treatment of asthmatic conditions it has been found to be effective to administer the compound in the form of dry powders or aerosols containing small particles of the medicament, conventionally prepared by micronization. However, the particle size of conventional formulations containing anhydrous beclomethasone dipropionate is known to increase on storage, due to solvate formation, to the extent that the medicament particles become too large to penetrate the bronchial system.

A number of potential solutions to this problem have been proposed. In dry powder compositions containing beclomethasone dipropionate it has been suggested that the problem may be overcome by using beclomethasone dipropionate in the form of its monohydrate (GB 2107715). In aerosol formulations, the use of micronized solvates of beclomethasone dipropionate, for example chlorofluorocarbon solvates (GB 1429184), ethyl acetate solvate (DE-3018550), $C_{5-8}$alkane solvates (EP-0039369), diisopropyl ether solvate (EP-0172672) and $C_{1-5}$ alcohol solvates (WO86/03750) has been proposed. GB 2076422 discloses a process for the preparation of chlorofluorocarbon aerosols which incorporates a low temperature (5° to −40° C.) step which is also claimed to inhibit crystal growth.

The presence of water in conventional aerosol formulations is known to be associated with a number of potential problems and it is generally accepted that these preparations should be maintained substantially free of water. The rigourous exclusion of atmospheric moisture during both the manufacture and storage of such formulations increases the difficulties of preparing satisfactory aerosols containing the drug and raises the overall cost of the final product.

SUMMARY OF THE INVENTION

We have now found that certain novel aerosol formulations containing beclomethasone dipropionate and water are surprisingly stable.

DESCRIPTION OF THE PREFERRED EMBODIMENTS

According to one aspect of the invention we provide an aerosol formulation comprising:

(a) beclomethasone dipropionate monohydrate, the particle size of substantially all the monohydrate being less than 20 microns;

b) at least 0.015% by weight of the formulation of water in addition to the water of crystallization associated with said monohydrate; and (c) a fluorocarbon or hydrogen-containing chlorofluorocarbon propellant.

Beclomethasone dipropionate monohydrate may be prepared by methods known in the art, for example as disclosed in GB 2107715. The particle size of the crystalline monohydrate may be reduced by conventional methods, for example by micronization and should be such as to permit inhalation of substantially all of the medicament into the lungs upon administration of the aerosol formulation. The particle size is thus desirably in the range of 1 to 10 microns e.g. 1 to 5 microns.

The final aerosol formulation desirably contains 0.005–10% w/w, preferably 0.005–5% w/w, especially 0.01–1.0% w/w. of beclomethasone dipropionate monohydrate relative to the total weight of the formulation.

The aerosol formulations according to the invention contain at least 0.015% (e.g. 0.015 to 0.1%) by weight of the formulation of water (excluding the water of crystallization associated with the beclomethasone dipropionate monohydrate), preferably at least 0.02%, for example 0.025% by weight or more of added water. Surprisingly, aerosol formulations of micronised beclomethasone dipropionate monohydrate and fluorocarbon or hydrogen-containing chlorofluorocarbon propellant, prepared substantially free of water e.g. less than 0.005% by weight, have been found to exhibit crystal growth on storage and are unacceptable. Preferred formulations according to the invention contain at least 0.026%, for example 0.026 to 0.08% by weight of water, in addition to the water of crystallization associated with the beclomethasone dipropionate monohydrate.

However, as will be appreciated by those skilled in the art the water solubility of individual fluorocarbon and hydrogen-containing chlorofluorocarbon propellants will not be identical and accordingly the minimum quantity of added water required to stabilize the aerosol formulations according to the invention will depend on the particular propellant used. Thus, for example, aerosol formulations comprising beclomethasone dipropionate monohydrate and 1,1,1,2-tetrafluoroethane as propellant preferably contain at least 0.026%, for example 0.03 to 0.08% by weight of added water. Aerosol formulations comprising beclomethasone dipropionate monohydrate and 1,1,1,2,3,3,3-heptafluoro-n-propane as propellant contain at least 0.015%, for example 0.02 to 0.05% by weight of added water.

The propellants for use in the invention may be any fluorocarbon or hydrogen-containing chlorofluorocarbon or mixtures thereof having a sufficient vapour pressure to render them effective as propellants. Preferably the propellant will be a non-solvent for the beclomethasone dipropionate monohydrate. Suitable propellants include, for example, $C_{1-4}$hydrogen-containing chlorofluorocarbons such as $C_2ClF$, $CClF_2CHClF$, $CF_3CHClF$, $CHF_2CClF_2$, $CHClFCHF_2$, $CF_3CH_2Cl$ and $CClF_2CH_3$; $C_{1-4}$hydrogen-containing fluorocarbons such as $CHF_2CHF_2$, $CF_3CH_2F$, $CHF_2CH_3$ and $CF_3CHFCF_2$; and perfluorocarbons such as $CF_3CF_3$ and $CF_3CF_2CF_3$.

Where mixtures of fluorocarbons or hydrogen-containing chlorofluorocarbons are employed they may be mixtures of the above identified compounds or mixtures, preferably binary mixtures, with other fluorocarbons or hydrogen-containing chloro- fluorocarbons for example $CHClF_2$, $CH_2F_2$ and $CF_3CH_3$. Preferably a single fluorocarbon or hydrogen-containing chlorofluorocarbon is employed as the propellant. Particularly preferred as propellants are $C_{1-4}$ hydrogen-containing fluorocarbons such as 1,1,1,2-tetrafluoroethene($CF_3CH_2F$) and 1,1,1,2,3,3,3-heptafluoro-n-propane ($CF_3CHFCF_3$).

It is desirable that the formulations of the invention contain no components which may provoke the degradation of stratospheric ozone. In particular it is desirable that the formulations are substantially free of chlorofluorocarbons especially non hydrogen-containing chlorofluorocarbons such as $CCl_3$, $CCl_2F_2$ and $CF_3CCl_3$. As used herein "substantially free" means less than 1% w/w based upon the fluorocarbon- or hydrogen-containing chlorofluorocarbon propellant, in particular less than 0.5%, for example 0.1% or less.

The propellant may optionally contain an adjuvant having a higher polarity and/or a higher boiling point than the propellant. Polar adjuvants which may be used include (e.g. $C_{2-6}$) aliphatic alcohols and polyols such as ethanol, isopropanol and propylene glycol, preferably ethanol. In general only small quantities of polar adjuvants (e.g. 0.05–3.0% w/w) may be required to improve the stability of the dispersion—the use of quantities in excess of 5% w/w may tend to dissolve the medicament. Formulations in accordance with the invention may preferably contain less than 1% w/w, e.g. about 0.1% w/w. of polar adjuvant. However, the formulations of the mention are preferably substantially free of polar adjuvants, especially ethanol. Suitable volatile adjuvants include saturated hydrocarbons such as propane, n-butane, isobutane, pentane and isopentane and alkyl ethers such as dimethyl ether. In general, up to 50% w/w of the propellant may comprise a volatile adjuvant, for example 1 to 30% w/w of a volatile saturated $C_{1-6}$ hydrocarbon.

Optionally, the aerosol formulations according to the invention may further comprise one or more surfactants. The surfactants must be physiologically acceptable upon administration by inhalation. Within this category are included surfactants such as oleic acid, sorbitan trioleate (Span®85), sorbitan mono-oleate, sorbitan monolaurate, polyoxyethylene (20) sorbitan monolaurate, polyoxyethylene (20) sorbitan mono-oleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl mono-oleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil and sunflower seed oil.

If desired, the surfactant may be incorporated into the aerosol formulation in the form of a surface coating on the beclomethasone dipropionate monohydrate particles. In this case, the use of substantially non-ionic surfactants Which have reasonable solubility in substantially non-polar solvents is frequently advantageous since it facilitates coating of the medicament particles using solutions of surfactant in non-polar solvents in which the medicament has limited or minimal solubility.

Thus according to a further aspect of the invention the aerosol formulations may be prepared by slurrying micron-ized beclomethasone dipropionate monohydrate with a solution of a surfactant such as lecithin in a substantially non-polar solvent (e.g. a lower alkane such as isopentane or a chlorofluorocarbon such as trichlorofluoromethane), optionally homogenising the slurry (e.g. by sonication), removing the solvent and if necessary simultaneously and/or subsequently breaking up the resulting solid cake, and dispersing the thus-obtained surfactant-coated particulate medicament in the chosen propellant in an appropriate aerosol container, e.g. with the aid of sonication. It may be preferred to add any cosolvent after the coated solvate and propellant have been combined, in order to minimise any solubilising effects of the cosolvent and thereby enhance the stability of the dispersion.

The amount of surfactant employed in coating the particulate medicament is desirably in the range 0.1 to 10% w/w, preferably 1 to 10% w/w, relative to the medicament. Where the surfactant is present as a surface coating, the amount may advantageously be chosen such that a substantially monomolecular coating of surfactant is formed.

However, it is preferable that the formulations of the invention are substantially free of surfactants.

A particularly preferred embodiment of the invention provides a pharmaceutical aerosol formulation consisting essentially of beclomethasone dipropionate monohydrate, at least 0.015% by weight of water and one or more fluorocarbon or hydrogen-containing chlorofluorocarbon propellant.

It will be appreciated by those skilled in the art that the aerosol formulations according to the invention may, if desired, contain one or more additional active ingredients. Aerosol compositions containing two active ingredients (in a conventional propellant system) are known, for example, for the treatment of respiratory disorders such as asthma. Accordingly the present invention further provides aerosol formulations in accordance with the invention which contain one or more additional particulate medicaments. Additional medicaments may be selected from any other suitable drug useful in inhalation therapy and which may be presented in a form which is substantially completely insoluble in the selected propellant. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or nedocromil; an antiinfectives e.g. cephalosporins, penicillins, streptomycin, sulphonamides, tetracyclines and pentamidine; antihistamines, e.g. methapyrilene; anti-inflammatories, e.g. fluticasone, flunisolide, budesonide, tipredane or triamcinolone acetonide; antitussives, e.g. noscapine; bronchodilators, e.g. satmeterol, salbutamol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, orciprenaline, or (−)-4-amino-3,5-dichloro-α-[[[6-[2-(2-pyridinyl)ethoxy]hexyl] amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or mine salts or as acid addition salts) or as esters (e.g. lower alkyl esters) or as solvates (e.g. hydrates) to optimise the activity and/or stability of the medicament and/or to minimise the solubility of the medicament in the propellant.

Particularly preferred aerosol formulations contain salbutamol (e.g. as the free base or the sulphate salt) or salmeterol (e.g. as the xinafoate salt) in combination with the beclomethasone dipropionate monohydrate. Combinations of salmeterol xinafoate and beclomethasone dipropionate monohydrate are preferred.

The formulations of the invention may be prepared by dispersal of the medicament and added water in the selected propellant in an appropriate container, e.g. with the aid of sonication.

The formulations according to the invention form weakly flocculated suspensions on standing but, surprisingly, these suspensions have been found to be easily redispersed by mild agitation to provide suspensions with excellent delivery characteristics suitable for use in pressurised inhalers, even after prolonged storage. Minimising and preferably avoiding the use of formulation excipients e.g. surfactants, cosolvents etc in the aerosol formulations according to the invention is also advantageous since the formulations may be substantially taste and odour free, less irritant and less toxic than conventional formulations.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The particle size distribution of the aerosol formulations according to the invention is particularly impressive and may be measured by conventional techniques, for example by cascade impaction or by the "Twin Impinger" analytical process. As used herein reference to the "Twin Impinger" assay means "Determination of the deposition of the emitted dose in pressurised inhalations using apparatus A" as defined in British Pharmacopaeia 1988, pages A204–207, Appendix XVII C. Such techniques enable the "respirable fraction" of the aerosol formulations to be calculated. As used herein reference to "respirable fraction" means the amount of naive ingredient collected in the lower impingement chamber per actuation expressed as a percentage of the total amount of active ingredient delivered per actuation using the twin impinger method described above. The formulations according to the invention have been found to have a respirable fraction of 20% or more by weight of the medicament, preferably 25 to 70%, for example 30 to 60%.

The formulations according to the invention may be filled into canisters suitable for delivering pharmaceutical aerosol formulations. Canisters generally comprise a container capable of withstanding the vapour pressure of the propellant used such as a plastic or plastic-coated glass bottle or preferably a metal can, for example an aluminium can which may optionally be anodised, lacquer-coated and/or plastic-coated, which container is closed with a metering valve. The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK356) and 3M-Neotechnic Ltd, UK (e.g. Spraymiser™).

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The particulate medicament and water is added to a charge vessel and liquified propellant is pressure filled through the charge vessel into a manufacturing vessel. The drug suspension is mixed before recirculation to a filling machine and an aliquot of the drug suspension is then filled through the metering valve into the canister. In an alternative bulk manufacturing method, the water is dissolved into the liquified propellant prior to the preparation of a suspension of-the drug in the water-containing propellant. The drug suspension is then pressure filled into the empty canisters in conventional manner. Typically, in batches prepared for pharmaceutical use, each filled canister is check-weighed, coded with a batch number and packed into a tray for storage before release testing.

Each filled canister is conveniently fined into a suitable channelling device prior to use to form a metered dose inhaler for administration of the medicament into the lungs or nasal cavity of a patient. Suitable channelling devices comprise for example a valve actuator and a cylindrical or cone-like passage through which medicament may be delivered from the filled canister via the metering valve to the nose or mouth of a patient e.g. a mouthpiece actuator. Metered dose inhalers are designed to deliver a fixed unit dosage of medicament per actuation or "puff", for example in the range of 10 to 5000 microgram medicament per puff.

Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1,2,3 or 4 puffs each time.

Suitable daily doses, may be, for example in the range 100 to 2000 microgram of beclomethasone dipropionate, depending on the severity of the disease.

Thus, for example, each valve actuation may deliver 50, 100, 200 or 250 microgram beclomethasone dipropionate. Typically each filled canister for use in a metered dose inhaler contains 100, 160 or 240 metered doses or puffs of medicament.

The filled canisters and metered dose inhalers described herein comprise further aspects of the present invention.

A still further aspect of the present invention comprises a method of treating respiratory disorders such as, for example, asthma, which comprises administration by inhalation of an effective amount of a formulation as herein described.

The following non-limitative Examples serve to illustrate the invention.

EXAMPLE 1

Micronized beclomethasone dipropionate monohydrate (68 mg), was weighed into a clean, dry, plastic-coated glass bottle together with water (6.1 mg). Dry (approximately 17 ppm $H_2O$) 1,1,1,2-tetrafluoroethane (to 18.2 g) was added from a vacuum flask. The bottle was quickly sealed with a metering valve. The resulting aerosol (330 ppm $H_2O$) dispensed 250 microgram beclomethasone dipropionate (as the monohydrate) per 75.8 mg actuation.

EXAMPLE 2

Micronized beclomethasone dipropionate monohydrate (52.2 g), water (44 ml) and 1,1,1,2-tetrafluoroethane (to 72.8 kg) were added to a pressure vessel and thoroughly mixed with a high shear mixer. Aliquots (18.2 g) of the suspension were filled into aluminium cans closed with a metering valve, filling under pressure through the valve using conventional filling equipment. The resulting inhalers contained 605 ppm added water and 13.04 mg beclomethasone dipropionate monohydrate. Each aerosol delivered 50 microgram beclomethasone dipropionate per 75.8 mg actuation.

EXAMPLE 3

Micronized beclomethasone dipropionate monohydrate (260.7 g) water (44 ml) and 1,1,1,2-tetrafluoroethane (to 72.8 kg) were added to a pressure vessel and thoroughly mixed with a high shear mixer. Aliquots (18.2 g) of the suspension were filled into aluminium cans closed with a metering valve, filling under pressure through the valve using conventional filling equipment. The resulting inhalers contained 605 ppm added water and 65.2 mg beclomethasone dipropionate monohydrate. Each aerosol delivered 250 microgram beclomethasone dipropionate per 75.8 mg actuation.

EXAMPLE 4

Micronized beclomethasone dipropionate monohydrate (62 mg) was weighed directly into an open aluminium can together with 6 microliters of water. A metering valve was then crimped into place and 1,1,1,2,3,3,3-heptafluoroethane (to 21.4 g) added to the canister under pressure through the valve. The resulting aerosol contained 280 ppm added water and dispensed 258.3 microgram beclomethasone dipropionate monohydrate per 89.2 mg actuation.

We claim:

1. A pharmaceutical aerosol formulation which comprises:
    (a) beclomethasone dipropionate monohydrate, the particle size of substantially all the monohydrate being less than 20 microns;
    (b) at least 0.015% by weight of the formulation of water in addition to the water of crystallisation associated with said monohydrate whereby said at least 0.015% water stabilizes the particle size of said beclomethasone dipropionate monohydrate particles;
    (c) a fluorocarbon or hydrogen-containing chlorofluorocarbon propellant.

2. A pharmaceutical aerosol formulation consisting essentially of particulate beclomethasone dipropionate monohydrate, at least 0.015% by weight of water and one or more fluorocarbon or hydrogen-containing chlorofluorocarbon propellant.

3. A formulation as claimed in claim 1 which comprises 0.015 to 0.1% by weight of added water.

4. A formulation as claimed in claim 1 which comprises at least 0.026% by weight of added water.

5. A formulation as claimed in claim 1 which comprises 0.026% to 0.08% by weight of added water.

6. A formulation as claimed in claim 1 wherein the propellant comprises a $C_{1-4}$ hydrogen-containing fluorocarbon.

7. A formulation as claimed in claim 6 wherein the propellant comprises 1,1,1,2,3,3,3-heptafluoro-n-propane.

8. A formulation as claimed in claim 6 wherein the propellant comprises 1,1,1,2-tetrafluoroethane.

9. A formulation as claimed in claim 1 which comprises 0.03 to 0.08% by weight of added water and 1,1,1,2-tetrafluoroethane as propellant.

10. A formulation as claimed in claim 1 which comprises 0.02 to 0.05% by weight of added water and 1,1,1,2,3,3,3-heptafluoro-n-propane as propellant.

11. A formulation as claimed in claim 1 wherein the beclomethasone dipropionate monohydrate is present in an amount of 0.005 to 10% w/w based on the total weight of the formulation.

12. A formulation as claimed in claim 1 which contains one or more additional active ingredients.

13. A formulation as claimed in claim 12 which comprises salmetermol or salbutamol or a physiologically acceptable salt thereof in combination with beclomethasone dipropionate monohydrate.

14. A formulation as claimed in claim 13 which comprises salbutamol and beclomethasone dipropionate monohydrate.

15. A formulation as claimed in claim 13 which comprises salmeterol xinafoate and beclomethasone dipropionate monohydrate.

16. A formulation as claimed in claim 1 which has a respirable fraction of 20% or more by weight of the medicament.

17. A process for preparing a pharmaceutical aerosol formulation as claimed in claim 1 which comprises dispersing the medicament and added water in propellant.

18. A method of treating respiratory disorders which comprises administration by inhalation of an effective amount of a pharmaceutical aerosol formulation which comprises:
    (a) beclomethasone dipropionate monohydrate, the particle size of substantially all the monohydrate being less than 20 microns;
    (b) at least 0.015% by weight of the formulation of water in addition to the water of crystallisation associated with said monohydrate whereby said at least 0.015% water stabilizes the particle size of said beclomethasone dipropionate monohydrate particles;
    (c) a fluorocarbon or hydrogen-containing chlorofluorocarbon propellant.

* * * * *